United States Patent
Tejidor et al.

(10) Patent No.: US 12,023,178 B2
(45) Date of Patent: Jul. 2, 2024

(54) METHOD OF DETECTING SEPSIS USING VITAL SIGNS, INCLUDING SYSTOLIC BLOOD PRESSURE, HEMATOLOGY PARAMETERS, AND COMBINATIONS THEREOF

(71) Applicant: Beckman Coulter, Inc., Brea, CA (US)

(72) Inventors: Liliana Tejidor, Coral Gables, FL (US); Robert T. Magari, Cooper City, FL (US); Diana Careaga, Miami, FL (US); Mohamad Hasan, Miami, FL (US)

(73) Assignee: Beckman Coulter, Inc., Brea, CA (US)

( * ) Notice: Subject to any disclaimer, the term of this patent is extended or adjusted under 35 U.S.C. 154(b) by 610 days.

(21) Appl. No.: 16/925,933

(22) Filed: Jul. 10, 2020

(65) Prior Publication Data

US 2021/0007675 A1    Jan. 14, 2021

Related U.S. Application Data

(60) Provisional application No. 62/927,835, filed on Oct. 30, 2019, provisional application No. 62/873,651, filed on Jul. 12, 2019.

(51) Int. Cl.
*G16H 50/50* (2018.01)
*A61B 5/00* (2006.01)
(Continued)

(52) U.S. Cl.
CPC .......... *A61B 5/7275* (2013.01); *A61B 5/0205* (2013.01); *G16H 10/40* (2018.01);
(Continued)

(58) Field of Classification Search
CPC ..... A61B 5/7275; A61B 5/0205; A61B 5/021; A61B 5/14546; G16H 10/40; G16H 10/60; G16H 50/20; G16H 50/30; G16H 50/50
See application file for complete search history.

(56) References Cited

U.S. PATENT DOCUMENTS 5,125,737 A    7/1992  Rodriquez et al.
5,341,291 A    8/1994  Roizen, III et al.
(Continued)

FOREIGN PATENT DOCUMENTS

CN    102033035 B    11/2013
EP       1021701       7/2000
(Continued)

OTHER PUBLICATIONS

Aird, William C., "The Hematologic System as a Marker of Organ Dysfunction in Sepsis", Mayo Clin Proc., Jul. 2003;78:869-881, 2003 Mayo Foundation for Medical Education and Research.
(Continued)

*Primary Examiner* — Carl H Layno
*Assistant Examiner* — Manolis Pahakis
(74) *Attorney, Agent, or Firm* — Frost Brown Todd LLP

(57) ABSTRACT

Using vital sign measurements, such as systolic blood pressure (SBP), when combined with hematology parameters such as White Blood Cell Count (WBC) and Monocyte Distribution Width (MDW), has been identified as an improved method for detecting sepsis. The probability of having or developing sepsis is determined when each measurement is compared to a predetermined criteria and the combination of measurements that are within a reference range determines this probability.

24 Claims, 6 Drawing Sheets

(51) Int. Cl.
  *A61B 5/0205* (2006.01)
  *G16H 10/40* (2018.01)
  *G16H 10/60* (2018.01)
  *G16H 50/20* (2018.01)
  *G16H 50/30* (2018.01)
  *A61B 5/021* (2006.01)
  *A61B 5/145* (2006.01)

(52) U.S. Cl.
  CPC .............. *G16H 10/60* (2018.01); *G16H 50/20* (2018.01); *G16H 50/30* (2018.01); *G16H 50/50* (2018.01); *A61B 5/021* (2013.01); *A61B 5/14546* (2013.01)

(56) References Cited

U.S. PATENT DOCUMENTS

| | | | |
|---|---|---|---|
| 5,529,933 | A | 6/1996 | Young et al. |
| 6,228,652 | B1 | 5/2001 | Rodriquez et al. |
| 6,509,192 | B1 | 1/2003 | Young |
| 7,109,036 | B2 | 9/2006 | Ortiz et al. |
| 7,135,341 | B2 | 11/2006 | Ortiz et al. |
| 7,176,031 | B2 | 2/2007 | Li et al. |
| 7,195,919 | B2 | 3/2007 | Jacobs et al. |
| 7,285,417 | B2 | 10/2007 | Ortiz et al. |
| 7,390,662 | B2 | 6/2008 | Riley et al. |
| 7,393,688 | B2 | 7/2008 | Ortiz et al. |
| 8,094,299 | B2 | 1/2012 | Wells et al. |
| 8,189,187 | B2 | 5/2012 | Graham et al. |
| 8,221,995 | B2 | 7/2012 | Lee et al. |
| 8,719,053 | B2 | 5/2014 | Showalter et al. |
| 9,939,453 | B2 | 4/2018 | Lu et al. |
| 10,221,453 | B2 | 3/2019 | Shi et al. |
| 2001/0051879 | A1 | 12/2001 | Johnson et al. |
| 2001/0051880 | A1 | 12/2001 | Schurenberg et al. |
| 2003/0105648 | A1 | 6/2003 | Schurenberg et al. |
| 2004/0042471 | A1 | 3/2004 | Yung et al. |
| 2004/0220761 | A1 | 11/2004 | Yundt-Pacheco |
| 2004/0267562 | A1 | 12/2004 | Fuhrer et al. |
| 2005/0022103 | A1 | 1/2005 | Yundt-Pacheco |
| 2005/0159982 | A1 | 7/2005 | Showalter et al. |
| 2008/0186134 | A1 | 8/2008 | Parkhurst et al. |
| 2009/0149724 | A1* | 6/2009 | Mark ................. A61B 5/0205 703/2 |
| 2011/0046910 | A1 | 2/2011 | Haas et al. |
| 2011/0076685 | A1 | 3/2011 | Moeller et al. |
| 2011/0166794 | A1 | 7/2011 | Linssen et al. |
| 2012/0109531 | A1 | 5/2012 | Knafel et al. |
| 2012/0109682 | A1 | 5/2012 | Seltzer et al. |
| 2013/0197943 | A1 | 8/2013 | Conlin et al. |
| 2013/0246079 | A1 | 9/2013 | Hoffman et al. |
| 2014/0160464 | A1 | 6/2014 | Han |
| 2014/0172321 | A1 | 6/2014 | Han |
| 2015/0338427 | A1 | 11/2015 | Pollack et al. |
| 2016/0168638 | A1 | 6/2016 | Garrett et al. |
| 2016/0356801 | A1 | 12/2016 | Glavina et al. |
| 2017/0285624 | A1 | 10/2017 | Lesher |
| 2018/0305758 | A1* | 10/2018 | Shi ........................ G01N 33/74 |
| 2019/0128906 | A1 | 5/2019 | Ramirez et al. |
| 2019/0324035 | A1* | 10/2019 | Magari ................. G16H 50/20 |
| 2019/0324036 | A1 | 10/2019 | Xin et al. |
| 2019/0348182 | A1 | 11/2019 | Magari et al. |
| 2019/0383800 | A1 | 12/2019 | Careaga et al. |
| 2020/0243171 | A1 | 7/2020 | Schmidt |
| 2021/0007675 | A1 | 1/2021 | Tejidor et al. |
| 2021/0010924 | A1 | 1/2021 | Tejidor et al. |
| 2021/0011005 | A1 | 1/2021 | Tejidor et al. |

FOREIGN PATENT DOCUMENTS

| | | |
|---|---|---|
| EP | 1718966 | 11/2006 |
| JP | 2012-529033 A | 11/2012 |
| KR | 20150036329 A | 4/2015 |
| KR | 20150091049 A | 8/2015 |
| WO | WO 88/07198 A1 | 9/1988 |
| WO | WO 2004/044556 A2 | 5/2004 |
| WO | WO 2012/139047 A2 | 10/2012 |
| WO | WO 2014/028534 A2 | 2/2014 |
| WO | WO 2014/084930 A1 | 6/2014 |
| WO | WO 2014/154810 A1 | 10/2014 |
| WO | WO-2017132132 A1 * 8/2017 ............. G16H 10/40 |
| WO | WO 2019/028448 | 2/2019 |

OTHER PUBLICATIONS

Anonymous, "Multiple Logistic Regression Analysis", Jan. 17, 2013, retrieved from http://sphweb.bumc.cu.edu/otlt/MPH-Modules/8S/8S704_Multivariable/8S704_Multivariables8.html.

Bhargava, et al. "Elevated mean neutrophil volume+ CRP is a highly sensitive and specific predictor of neonatal sepsis", Letter to the Editor, International Journal of Laboratory Hematology, DOI: 10.1111/iijh.12120, 2013, 4 pages.

"Biomarker," The Pharmaceutical Society of Japan, a pharmaceutical science glossary, 2008, 2 pgs.

Celik, et al., "Automated determination of neutrophil VCS parameters in diagnosis and treatment efficacy of neonatal sepsis", Pediatric Research, vol. 71, No. 1, Jan. 2012, pp. 121-125.

Chaves, et al. "Neutrophil Volume Distribution Width: A New Automated Hematologic Parameter for Acute Infection", Arch Pathol Lab Med, vol. 130. Mar. 2006, pp. 378-380.

Chaves, et al. Quantitative Determination of Neutrophil VCS Parameters by the Coulter Automated Hematology Analyzer: New and Reliable Indicators for Acute Bacterial Infection. American Journal Clinical Pathology, 2005, 124:440-444.

Cho, et al., "Biomarkers of Sepsis", Infection & Chemotherapy, Feb. 2014; 46:1-12.

Crouser, et al., "Improved Early Detection of Sepsis in the ED with a Novel Monocyte Distribution Width Biomarker", 152#3 Chest, Sep. 2017, pp. 518-526.

Dellinger, et al. "Surviving Sepsis Campaign: International Guidelines for Management of Severe Sepsis and Septic Shock, 2012", Intensive Care Medicine, 2013, 39:164-228.

Dilmoula, et al., "Volume, Conductivity and Scatter Properties of Leukocytes (VCS Technology) in Detecting Sepsis in Critically Ill Adult Patients", Blood (ASH annual Meeting Abstracts) 2011; 118: Abstract 4729, 3 pages.

Early Sepsis Indicator Application Addendum UniCel DxH 900 Coulter Cellular Analysis System, Beckman Coulter, published Version: v1, Available online at: https://www.analis.be/site/objects/media/0/0/8/1/9/0081990_media/medial.pdf, Apr. 26, 2018, 38 pages.

Ferrer, et al., "Emperic Antibiotic Treatment Reduces Mortality in Severe Sepsis and Septic Shock from the First Hour: Results from a Guideline-Based Performance Improvement Program", Critical Care Medicine, Aug. 2014, vol. 42, No. 8, pp. 1749-1755.

Gaieski, et al., "Impact of time to antibiotics on survival in patients with severe sepsis or septic shock in whom early goal-directed therapy was initiated in the emergency department", Critical Care Medicine, 2010, vol. 38, No. 4, pp. 1045-1053.

Garnacho-Montero, et al., "Impact of adequate empirical antibiotic therapy on the outcome of patients admitted to the intensive care unit with sepsis", Critical Care Medicine, 2003;31 :2742-51.

Gea-Banecloche, et al. "Sepsis associated with immunosuppressive medications: An evidence-based review" Critical Care Medicine 2004; 32:S578-S590.

Glickman, et al., Disease Progression in Hemodynamically Stable Patients Presenting to the Emergency Department with Sepsis. Academic Emergency Medicine, vol. 17, Issue 4, Apr. 2, 2010, pp. 383-390.

Goyette, et al., "Hematologic changes in sepsis and their therapeutic implications," Seminars in Respiratory and Critical Care Medicine, vol. 25, No. 6, pp. 645-659 (2004).

Hou, et al., Viral infection triggers rapid differentiation of human blood monocytes into dendritic cells, Blood, Mar. 29, 2012, vol. 119, No. 12, pp. 3128-3132.

Kaukonen, et al., "Systemic Inflammatory Response Syndrome Criteria in Defining Severe Sepsis," New England Journal of Medicine, 372: 1629-38, Apr. 23, 2015, (doi:610.1056/NEJMoa1415236).

(56) References Cited

OTHER PUBLICATIONS

Lee, et al., "Mean cell volumes of neutrophils and monocytes are promising markers of sepsis in elderly patients", Blood Research, vol. 48, No. 3, Sep. 2013, 5 pages.
Levy, et al., "2001 SCCM/ESICM/ACCP/ATS/SIS Sepsis Definitions Conference", Critical Care Medicine, Mar. 28, 2003, 29: 530-538.
Liu, et al., "Hospital Deaths in Patients with Sepsis from 2 Independent Cohorts", JAMA Jul. 2, 2014; 312: 90-92.
Mardi, et al., Mean cell volume of neutrophils and monocytes compared with C-reactive protein, interleukin-6 and white blood cell count for prediction of sepsis and nonsystemic bacterial infections, accepted for publication, Sep. 23, 2009, International Journal of Laboratory Hematology 2010;32:410-418.
Park, et al., "Screening of sepsis using leukocyte cell population data from the Coulter automatic blood cell analyzer DxH800", International Journal of Laboratory Hematology, Dec. 6, 2010, 9 pages.
Raimondi, et al., "Automated Determination of Neutrophil Volume as Screening Test for Late-Onset Sepsis in Very Low Birth Infants", Pediatric Infectious Disease Journal, Feb. 2010; 29:288-89.
"Red Blood Cell Distribution With (RDW): Definition and Calculation—LabCE.com, Laboratory Continuing Education," Nov. 2012, downloaded Aug. 22, 2019 from: https://labce.com/spg579122_red_blood_cell_distribution_width_rdw_definition_a.aspx, 1 pg.
Seymour, et al. "Severe Sepsis in Pre-Hospital Emergency Care: Analysis of Incidence, Care, and Outcome", American Journal of Respiratory Critical Care Medicine, Dec. 15, 2012; 186:1264-71.
Shalova, et al., "Human Monocytes Undergo Functional Reprogramming during Sepsis Mediated by Hypozia-Inducible Factor-1a", Immunity, Mar. 17, 2015; 42:484-98.
Singer, et al., "The Third International Consensus Definitions for Sepsis and Septic Shock (Sepsis-3)," JAMA, 10 315(8): 801-810, Feb. 23, 2016.
Skibsted, et al., "Bench-to-bedside review: Future novel diagnostics for sepsis—a systems biology approach", Critical Care Oct. 4, 2013;17:231, 15 pages.
Sukhacheva, et al., "The Role of Monocytes in the Progression of Sepsis," Beckman Coulter, 2018, downloaded Aug. 22, 2019 from: media.beckmancoulter.com/-/media/diagnostics/products/hematology/early-sepsis-indicator/docs/role-of-monocytes-for-progression-of-sepsis-en.pdf, 12 pgs.
Torio, et al., "National Inpatient Hospital Costs: The Most Expensive Conditions by Payer, 2011", H-Cup US, Aug. 2013, 8 pages, retrieved from: https://www.hcup-us.ahrq.gov/reports/statbriefs/sb160.jsp.
"UniCel DxH 800—Coulter Cellular Analysis System", Available online at: https://www.udh.med.sa/advices/DxH_operator_Manual.pdf, Aug. 5, 2017, 54 pages.
Vis, et al., "Verification and Quality Control of Routine Hematology Analyzers" International Journal of Laboratory Hematology, vol. 38, No. 1, May 9, 2016, pp. 100-109.
Warner, "Tips for evaluating a peripheral blood smear for possible sepsis," Jan. 15, 2013, 3 pages, available at laboratorian.advanceweb.com/signs-of-sepsis/.
Zhou, et al., "VCS parameters of neutrophils, monocytes and lymphocytes may indicate local bacterial infection in cancer patients who accepted cytotoxic chemotherapeutics," Eur J Clin Microbiol Infect Dis, 2016, 35:41-48, 8 pgs.
Zonneveld, R., et al., "Analyzing Neutrophil Morphology, Mechanics, and Motility in Sepsis: Options and Challenges for Novel Bedside Technologies," Crit Care Med, 2016, 44(1):218-228, 11 pgs.
European Examination Report dated Oct. 15, 2020 for Application No. EP 17704357.7, 10 pgs.
International Search Report and Written Opinion dated Apr. 20, 2017 for International Application No. PCT/US2017/014708, 16 pages.
International Search Report and Written Opinion dated May 4, 2018 for International Application No. PCT/US2018/020087, 13 pages.
International Search Report and Written Opinion dated Mar. 26, 2019 for International Application No. PCT/US2018/057645, 16 pages.
International Search Report and Written Opinion dated Sep. 4, 2019 for International Application No. PCT/US2019/028486, 11 pgs.
International Search Report and Written Opinion dated Aug. 2, 2019 for International Application No. PCT/US2019/028487, 7 pages.
International Search Report and Written Opinion dated Aug. 23, 2019 for International Application No. PCT/US2019/028488, 10 pgs.
International Search Report and Written Opinion dated Aug. 20, 2019 for International Application No. PCT/US2019/031151, 9 pages.
International Search Report and Written Opinion dated Oct. 20, 2020 for International Application No. PCT/US2020/041535, 12 pgs.
International Search Report and Written Opinion dated Oct. 8, 2020 for International Application No. PCT/US2020/041548, 10 pgs.
International Search Report and Written Opinion dated Oct. 5, 2020 for International Application No. PCT/US2020/041541, 10 pgs.
Japanese Office Action, Notice of Reasons for Refusal, dated Oct. 29, 2020 JP 2018-538892, 27 pgs.
U.S. Office Action, Restriction Requirement, dated Apr. 7, 2021 for U.S. Appl. No. 15/987,541, 5 pgs.
U.S. Office Action, Non-Final Rejection, dated Jul. 31, 2020 for U.S. Appl. No. 16/073,757, 23 pgs.
U.S. Office Action, Notice of Allowance, dated Feb. 8, 2021 for U.S. Appl. No. 16/073,757, 20 pgs.
Beckman Coulter, "Coulter® 3-D VCS Technology," from <http://www.cyto.purdue.edu/cdroms/cyto2/6/coulter/ss000125.htnn> (Year: 1996).
Beckman Coulter, Early Sepsis Indicator (ESId) Application for UniCel DxH 900 Series with System Manager Software, PN C26693AC (Jun. 2019), <https://www.beckmancoulter.corn/download/file/wsr-308328/C26693AC?type=pdf> (Year: 2019).
Beckman Coulter, Early Sepsis Indicator (ESId) Application Addendum, UniCel DxH 900 Series with System Manager Software Coulter Cellular Analysis System, PN C42014AC (Apr. 2020), <https://www.beckmancoulter.com/download/file/wsr-292218/C42014AC?type=pdf> (Year: 2020).
Beckman Coulter, UniCel DxH 900 Series with System Manager Software, PN B26647AG, <https://www.beckmancoulter.corn/download/file/wsr-156667/B26647AG?type=pdf> (Year: 2020).
Cembrowski, George S., B. Smith, and D. Tung. "Rationale for using insensitive quality control rules for today's hematology analyzers." *International Journal of Laboratory Hematology* 32.6p2 (2010): 606-615.
FDA 510(k) Substantial Equivalence Determination Decision Summary, <https://www.accessdata.fda.gov/cdrh_docs/reviews/K181599.pdf> (Year: 2018).
Nachimuthu, Senthil K., and Peter J. Haug. "Early detection of sepsis in the emergency department using Dynamic Bayesian Networks." *AMIA Annual Symposium Proceedings*. vol. 2012. American Medical Informatics Association, 2012.
Petrak, Russel M., et al. "The value of an infectious diseases specialist." *Clinical infectious diseases* 36.8 (2003): 1013-1017.
Chinese Office Action dated May 31, 2021, for Application No. 201780006733.8, 14 pages.
Chinese Office Action dated Mar. 9, 2022, for Application No. 201780006733.8, 4 pages.
European Examination Report dated Nov. 27, 2020, for Application No. 18712041.5, 11 pages.
European Examination Report dated Jul. 12, 2022, for Application No. 18845383.1, 13 pages.
Indian Office Action dated Jun. 25, 2021, for Application No. 201817031635, 7 pages.
Japanese Notification of Reasons for Refusal dated Feb. 4, 2022, for Application No. 2021-012832, 4 pages.
Japanese Notification of Reasons for Refusal dated Jun. 17, 2022, for Application No. 2021-012832, 2 pages.
Korean Office Action dated Aug. 27, 2021, for Application No. 10-2018-7024386, 27 pages.

(56) References Cited

OTHER PUBLICATIONS

U.S. Non-Final Rejection dated Jul. 9, 2021, for U.S. Appl. No. 15/987,541, 15 pages.
U.S. Final Rejection dated Feb. 17, 2022, for U.S. Appl. No. 15/987,541, 14 pages.
U.S. Notice of Allowance dated Sep. 1, 2022, for U.S. Appl. No. 15/987,541, 8 pages.
U.S. Restriction Requirement dated May 2, 2022, for U.S. Appl. No. 16/170,389, 7 pages.
U.S. Non-Final Rejection dated Aug. 1, 2022, for U.S. Appl. No. 16/170,389, 21 pages.
U.S. Restriction Requirement dated Mar. 14, 2022, for U.S. Appl. No. 16/390,597, 6 pages.
U.S. Non-Final Rejection dated Jun. 13, 2022, for U.S. Appl. No. 16/390,597, 8 pages.
U.S. Non-Final Rejection dated Jul. 2, 2021, for U.S. Appl. No. 16/390,633, 9 pages.
U.S. Non-Final Rejection dated Feb. 25, 2022, for U.S. Appl. No. 16/390,633, 13 pages.
U.S. Final Rejection dated Aug. 9, 2022, for U.S. Appl. No. 16/390,633, 11 pages.
U.S. Non-Final Rejection dated Jul. 9, 2021, for U.S. Appl. No. 16/390,648, 15 pages.
U.S. Final Rejection dated Feb. 17, 2022, for U.S. Appl. No. 16/390,648, 14 pages.
U.S. Notice of Allowance dated Jun. 15, 2022, for U.S. Appl. No. 16/390,648, 7 pages.
U.S. Restriction Requirement dated Jun. 16, 2021, for U.S. Appl. No. 16/488,503, 8 pages.
U.S. Non-Final Rejection dated Nov. 24, 2021, for U.S. Appl. No. 16/488,503, 21 pages.
U.S. Final Rejection dated Aug. 11, 2022, for U.S. Appl. No. 16/488,503, 21 pages.
U.S. Restriction Requirement dated Aug. 8, 2022, for U.S. Appl. No. 16/925,937, 13 pages.
U.S. Restriction Requirement dated Oct. 5, 2022, for U.S. Appl. No. 16/925,943, 8 pages.

* cited by examiner

METHOD OF DETECTING SEPSIS USING VITAL SIGNS, INCLUDING SYSTOLIC BLOOD PRESSURE, HEMATOLOGY PARAMETERS, AND COMBINATIONS THEREOF

CROSS-REFERENCES TO RELATED APPLICATIONS

This is related to, and claims the benefit of, provisional patent application 62/873,651, titled "method of detecting sepsis using vital signs, including systolic blood pressure, hematology parameters, and combinations thereof" filed in the United States Patent Office on Jul. 12, 2019, as well as provisional patent application 62/927,835, titled "method of detecting sepsis using vital signs, including systolic blood pressure, hematology parameters, and combinations thereof" filed in the United States Patent Office on Oct. 30, 2019. This application is related by subject matter to PCT Patent Application No. PCT/US17/14708, titled "Infection Detection and Differentiation Systems and Methods," filed Jan. 24, 2017, which claims the benefit of U.S. Provisional Patent Application No. 62/288,091, titled "Infection Detection and Differentiation Systems and Methods," filed Jan. 28, 2016. This application is also related to U.S. Provisional Application No. 62/660,795, titled "Sepsis Infection Detection Systems and Methods," filed Apr. 20, 2018.

FIELD

The present disclosure relates to methods for detecting an infection, including infections resulting in sepsis, by using vital signs combined with parameters measured by a hematology analyzer. Measuring systolic blood pressure alone or in combination with additional hematology parameters has been found to improve sepsis predictive accuracy.

BACKGROUND

Sepsis is a systemic inflammatory response to an infection that can quickly spiral into a life-threatening condition. Patient mortality increases by 8% with each hour that passes without diagnosis, and treatment. In the past, the diagnosis of sepsis has been hindered from lack of a clear definition and both timely and accurate diagnosis. Sepsis is now the number 1 cost of hospitalization, and $3^{rd}$ leading cause of death in the United States alone.

In 1992 the first definition of sepsis was published, in which systemic inflammatory response syndrome (SIRS) was proposed to define the condition. SIRS occurs when two or more of the following criteria are met: a temperature greater than 38 degrees Celsius (C) or less than 36 degrees C., a heart rate greater than 90 beats per minute (bpm), a respiratory rate greater than 20 breaths per minute (breaths/min), or a white blood cell count (WBC) less than 4,000 per microliter of blood (4,000/mm$^3$) (leukopenia) or greater than 12,000/mm$^3$ (leukocytosis). At the time, sepsis was defined as a condition which occurs when 2 or more SIRS criteria are met, and an infection persists in the body. However, the condition of sepsis is still not well understood, and this definition has subsequently undergone alterations. In 2016 this definition, "Sepsis-2," was updated and is now referred to as "Sepsis-3," which in includes organ dysfunction. Instead of SIRS, a "sequential organ failure assessment" (SOFA) was proposed which, due to its extensiveness, is often initially evaluated by a quick SOFA (qSOFA) first. In a hospital setting, a quick sequential organ failure assessment is administered first. If a qSOFA indicates that a patient is at risk of sepsis, then a full SOFA test may be administered.

Like SIRS, qSOFA also assesses patient vital signs. With a sensitivity as much as 84%, SIRS is far more sensitive than qSOFA which has a sensitivity of 49%. However, at 79%, qSOFA has a much higher specificity than SIRS which is about 35% specific for sepsis. Despite its high sensitivity, SIRS has still been shown to leave out about 12.5% of patients with sepsis (1 in 8) who did not test positive for at least 2 SIRS criteria. Neither qSOFA nor SIRS have sufficient performance to consistently help health professionals identify sepsis early and without waiting for any laboratory results. Furthermore, if a patient does not present outward signs of inflammation, it might not be apparent to utilize these criteria. This is crucial, as these signs may not be displayed for several, critical hours.

Biomarkers, such as procalcitonin (PCT) and C-reactive protein (CRP), have previously been identified as another tool capable of indicating sepsis, yet such biomarkers still lack the specificity and sensitivity to detect all sepsis cases. PCT, with a sensitivity and specificity of about 75% and 79%, respectively, is widely thought to be the most reliable of these biomarkers yet can still yield both false positive and false negative results. Additionally, PCT cannot consistently differentiate sepsis from non-infectious cases. PCT is further hindered by cost and is only ordered by a clinician when the patient is already showing outward signs of inflammation. There can be a significant delay before a patent shows signs of inflammation, especially in particular infections where organ dysfunction does not generate a systemic host response. These factors prevent the use of PCT for early diagnosis of sepsis, and a patient may be in life-threatening condition before the test is ordered.

An increased WBC is, in general, associated with bacterial infection, but a significant patient population has been shown not to exhibit this change, thus leaving out a critical number of at-risk patients. Furthermore, elevated WBC is associated with a variety of other conditions such as trauma or severe burn, so WBC alone is not useful in sepsis diagnosis. Other laboratory tests including complete blood count with differential (CBC-diff), serum lactate, erythrocyte sedimentation rate (ESR), and bacterial cultures have also been used in the past to diagnose sepsis, but also lack sufficient specificity and sensitivity, and can be further hindered by the high cost or the length of time that it takes to complete these tests.

More recently, an additional hematology analyzer parameter, monocyte distribution width (MDW), has been shown to indicate sepsis, with a sensitivity and specificity of 74% and 72%, respectively, and is especially efficacious when combined with other measurements associated with infection, such as WBC. The use of this tool is particularly advantageous, as this value is measured on all patient samples, therefore these hematology parameters may be useful in detecting sepsis even before a patient displays outward signs of inflammation. However, there is still a need to improve the specificity and sensitivity of laboratory testing for sepsis to further reduce the number of patients who experience delayed diagnosis and treatment.

For these and other reasons, improved methods or systems for identifying infection and sepsis, are desirable.

BRIEF SUMMARY

In the past, the assessment of sepsis, or the probability of developing sepsis, has been hindered by a lack of a clear definition and a timely diagnostic tool that is acceptably sensitive and specific. In addition to SIRS criteria and various biomarkers, sepsis may be assessed in part by evaluating the MDW measured from a blood sample. Exemplary methods are disclosed, for example, in PCT Patent Application No. PCT/US17/14708 and U.S. Provisional Application No. 62/660,795. Embodiments of present disclosure may improve the predictive ability of MDW through combination with WBC and vital signs. A system to evaluate the infection status may involve any of the methods described herein.

According to a first aspect, some embodiments may provide a method of assessing a probability that a patient will develop sepsis. In some embodiments, such a method may comprise, at a data processing system, receiving measurements comprising a white blood cell count (WBC), a monocyte distribution width (MDW), and one or more vital signs. In some embodiments, such a method may comprise the data processing system processing the received measurements to (i) determine whether each measurement meets a corresponding predetermined criteria and (ii) assign the probability that the patient will develop sepsis.

According to a second aspect, in some embodiments according to the first aspect, the patient may be assigned a risk of developing sepsis if, for each of two or more measurements, including at lest one of the one or more vital signs: (a) the corresponding predetermined criteria for that measurement is a predetermined range; and (b) that measurement is within its corresponding predetermined range.

According to a third aspect, in some embodiments according to any of the first or second aspects, the one or more vital signs may comprise blood pressure.

According to a fourth aspect, in some embodiments according to any of the first through third aspects, the one or more vital signs may comprise systolic blood pressure (SBC).

According to a fifth aspect, in some embodiments according to the fourth aspect, the predetermined criteria for SBP may be a value of or below about 100 mmHg.

According to a sixth aspect, in some embodiments according to any of the first through fifth aspects, at least one measurement may be received from an electronic medical record and at least one measurement may be received from an analyzer.

According to a seventh aspect, in some embodiments according to any of the first through sixth aspects, the predetermined criteria for MDW may be a value above 20.0 channels.

According to an eighth aspect, in some embodiments according to any of the first through seventh aspects, the predetermined criteria for WBC may be a value less than about $4.0 \times 10^3/\mu L$ or greater than about $12.0 \times 10^3/\mu L$.

According to a ninth aspect, in some embodiments according to any of the first through seventh aspects, the predetermined criteria for WBC may be a value less than about $5.0 \times 10^3/\mu L$, or greater than about $10.0 \times 10^3/\mu L$.

According to a tenth aspect, in some embodiments according to any of the first through ninth aspects, at least one of the one or more vital signs may be a SIRS or qSOFA vital sign measurement.

According to an eleventh aspect, in some embodiments according to any of the first through tenth aspects, at least one of the predetermined criteria may be a SIRS or qSOFA vital sign criteria.

According to a twelfth aspect, in some embodiments according to any of the first through eleventh aspects, the measurements may be measurements taken within 12 hours of patient presentation.

According to a thirteenth aspect, in some embodiments according to any of the first through eleventh aspects, the measurements may comprise measurements taken 12 or more hours after patient presentation.

According to a fourteenth aspect, some embodiments may provide a computer readable medium having instructions operable to, when executed, cause a data processing system to perform the method of any of the first through thirteenth aspects.

According to a fifteenth aspect, some embodiments may provide a data processing system configured with instructions to perform the method of any of the first through thirteenth aspects.

DETAILED DESCRIPTION

Figure 1:
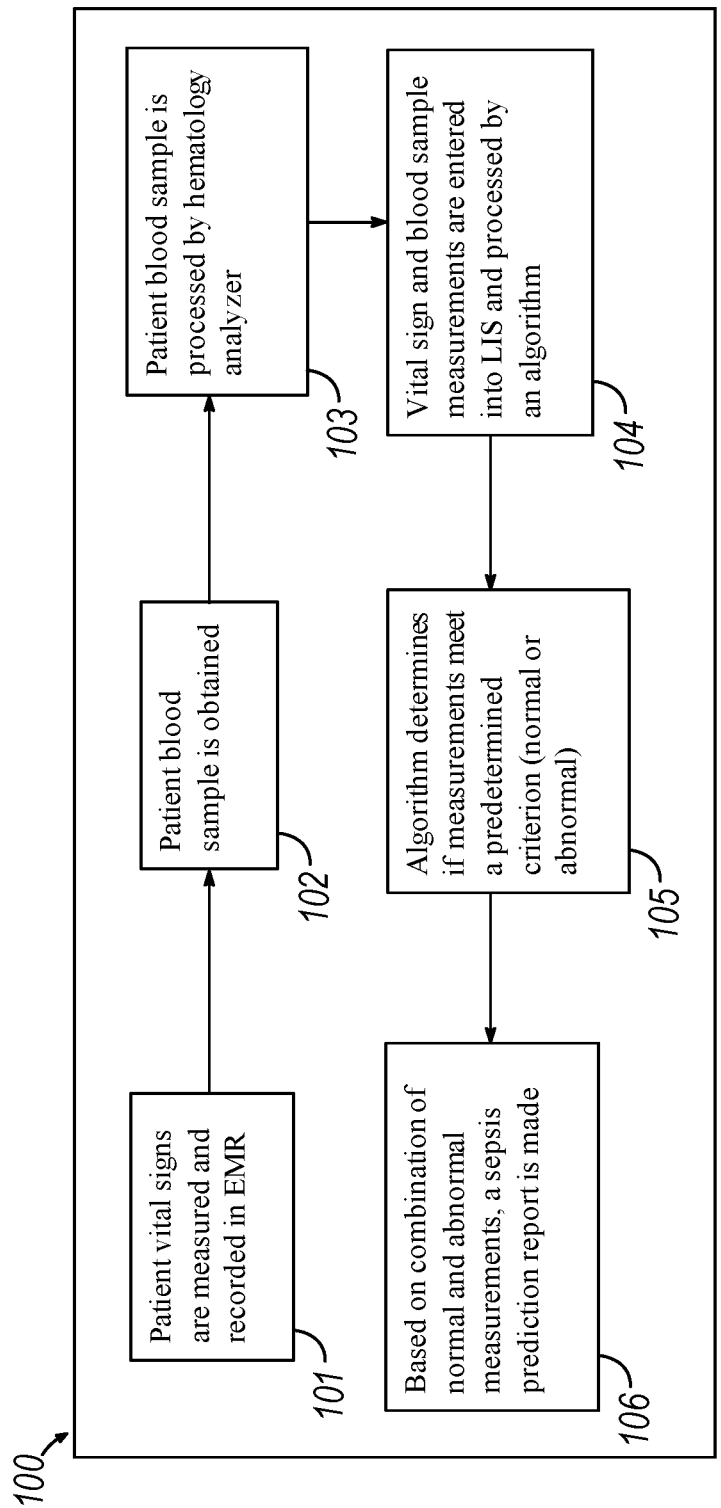
FIG. 1 provides a simplified block diagram of an exemplary infection detection method, according to embodiments of the present disclosure.

Sepsis is a systemic inflammatory response to an infection that can become life-threatening. Sepsis arises when the body's response to an infection is out of balance, and the chemicals released into the bloodstream to fight an infection lead to inflammation and severely injure the body's own tissues and organs. In the most severe cases, this can lead to septic shock (at this time, also referred to as "sepsis-3"), where circulatory and cellular damage drastically increase mortality.

Sepsis is a complicated condition and is continuously being redefined. In 2016, the Third International Consensus Definitions for sepsis and sepsis were redefined. Due to poor specificity and sensitivity SIRS was replaced by SOFA which, due to its extensiveness, is initially evaluated by a qSOFA score. A qSOFA is scored on a scale from 0-3 points, with 1 point for each vital sign that tests positively. These qSOFA vital sign criteria are a respiratory rate of >22 breaths/min, systolic arterial blood pressure of less than or equal to 100/mmHg, and an altered mental status (Glasgow Coma Scale score below 15). It has been determined that patients with a qSOFA score of at least 2 have a 24% in-hospital mortality rate, and 3% for patients with a qSOFA score of less than 2. Typically, if the qSOFA score is of at least 2, then the patent will be evaluated with the full SOFA test. The SOFA test is scored on a scale of 0-24 and involves evaluating specific organ systems (respiratory, cardiovascular, liver, renal, coagulation, and central nervous system). If the SOFA score is also greater than or equal to 2, then the patient is considered septic.

Though not initially meant to be a replacement for SIRS, but rather an early detection method, the use of qSOFA has been an improvement over SIRS criteria in general. SIRS, developed in 1991, has a high sensitivity, but with very low specificity. SIRS criteria, which may also be referred to as SIRS vital sign criteria or SIRS vital sign measurement, are: a temperature greater than 38 degrees C. (fever), or less than 36 degrees C. (hypothermia), a heart rate greater than 90 beats/minute (tachycardia), a respiratory rate greater than 20 breaths/min (tachypnea), and a WBC less than 4,000 per microliter of blood (4,000/mm$^3$) (leukopenia) or greater than 12,000/mm$^3$ (leukocytosis). Previous studies have shown that nearly 75% of patients presenting to the emergency department (ED) with suspected infection were shown to have at least 2 SIRS points, but very few had severe organ dysfunction. Similarly, other studies have reported that 68 to 93% of patients admitted in the ICU, in general, had at least two elements of SIRS. This indicates that having two or more elements of SIRS does not discriminate well enough for organ dysfunction. This is considered to be widely due to the fact that changes in temperature, heart rate, respiratory rate or WBC are typical body responses to many infections and illnesses, not necessarily a life-threatening organ failure or dysregulated body response. Despite this high sensitivity, 1 in 8 septic patients still does not test positively for sepsis with SIRS criteria.

While qSOFA may be an improvement over SIRS criteria, the American Medical Association (AMA) has noted that there are still considerable drawbacks. The qSOFA was developed for patients already suspected of having an infection, meaning that it is not meant to be an alert which can itself discern between patients with or without an infection but, rather, was defined to identify patients most likely to die. The qSOFA score has poor sensitivity for early sepsis indication but, rather, serves to identify patients who are among the most ill and with higher mortality risk. Second, altered mental status, which may also be referred to as AMS or sepsis-associated delirium (SAD), is a subjective measurement and can vary clinically. Finally, qSOFA does not include any blood measurements that have previously been shown to be effective for screening sepsis, such as WBC.

The present disclosure relates to methods for detecting an infection, including infections resulting in sepsis, by using vital signs combined with parameters measured by a hematology analyzer. Measuring systolic blood pressure (SBP), a vital sign, has been found to improve sepsis prediction accuracy, especially when combined with parameters measured by a hematology analyzer. When combined with abnormal MDW and WBC, other qSOFA or SIRS vital sign measurements have also been found to improve sepsis detection, including altered mental status, temperature, heart rate, respiratory rate, and combinations of these criteria, such as heart rate together with respiratory rate. Furthermore, the benefit of these methods has been observed using only the vital sign measurements collected in the early stages of patient triage, beginning within the first hours of presentation. This includes measurements taken in any of the first 0-12 hours of presentation. Further benefit may be attained by including measurements made beyond the first 12 hours of presentation. Patient presentation may be to any medical setting including hospital ED, emergency vehicle, critical care center, in-patient care facility, out-patient care facility, hospice home, specialty clinic, long-term patient care facility, senior home, rehabilitation center, urgent care, telehealth, or specialty treatment center, for example.

FIG. 1 schematically depicts an embodiment of an infection detection method 100 according to the present disclosure. In this embodiment, a patient's vital signs may be measured and recorded in EMR 101, and a blood sample obtained 102. This blood sample may then be processed by a hematology analyzer 103. Vital sign and blood sample measurements may be input into a laboratory information system (LIS) for processing either manually or automatically 104. These measurements may be obtained by the LIS from a patient record, such as an electronic medical record (EMR) or from a laboratory instrument, otherwise referred to as analyzer. These measurements may be obtained during early patient triage. Early patient triage may be defined by the first measurement of a patient's vital signs by a trained professional and may include the first 0-12 hours of patient presentation. Patient presentation occurs on arrival of a patient to a medical setting and may be marked by the time in which a patient has been registered clerically or, in emergency situations, the time in which a patient is triaged. Patient presentation may also refer to the moment a patient is introduced to a trained professional in a medical setting. A medical setting may include a hospital ED, emergency vehicle, critical care center, in-patient care facility, out-patient care facility, hospice home, specialty clinic, long-term patient care facility, senior home, rehabilitation center, urgent care, telehealth, or specialty treatment center. A trained professional may include physicians, nurses, therapists, physician assistants, hospice workers, emergency medical technicians, and any other trained caregivers. In the examples disclosed herein, the first measurement of vital signs by a trained professional was, on average, executed within 2 hours after introduction to a nurse in the ED. The blood sample measurements may include WBC and MDW. The vital sign measurements may include any SIRS or qSOFA vital sign measurement. The vital sign measurements may include a blood pressure measurement. In some aspects, the LIS includes a processor and a non-transitory computer readable storage medium. The computer readable medium may be programmed with an application to cause the processor to evaluate inputted measurements to determine whether each measurement meets a predetermined criterion, based on an algorithm 105. Based on which of the predetermined criteria is met for the inputted measurements, the probability that a patient will develop sepsis may be determined 106. The predetermined criteria for these measurements may be a range of values considered to be abnormal for a healthy adult, and predictive of developing sepsis alone or in combination with other measurements.

Figure 2:
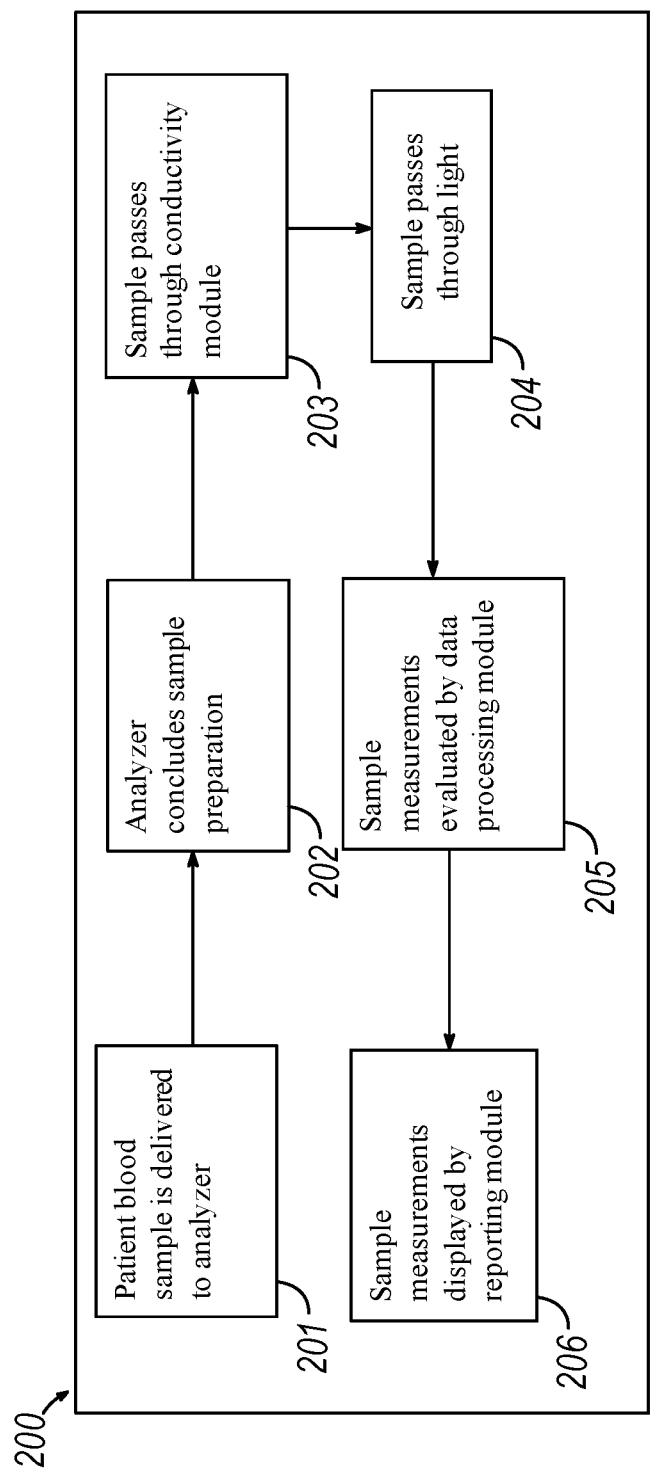
FIG. 2 provides a flowchart of an exemplary hematology analyzer process.

As stated, these measurements may be extracted from an EMR by a LIS. An EMR is a real-time, comprehensive collection of patent data including medical history, physician notes, diagnoses, medication, allergies, immunizations, laboratory test results and vital signs. A LIS is a software system that stores, processes, and manages laboratory analyzer data, and patient information, including patient sample measurements. Laboratory test results derived from a patient biological sample, such as WBC and MDW, may also be input to the LIS manually, by a laboratory professional, or directly from an analyzer. An analyzer is a clinical diagnostic machine capable of measuring one or more anatomical or physiological properties of a sample, including: metabolic measurements (also referred to as blood chemistry); cell counts; viral protein, viral gene or microbial cell measurements; urine measurements; genomic characterizations; or immunological measurements. FIG. 2 schematically depicts an exemplary hematology analyzer process 200. In this embodiment, a patient's blood sample may be delivered to the analyzer 201, at which point the analyzer may prepare the sample for analysis. Once the sample preparation is concluded 202, the sample may pass through a conductivity module 203 and light scatter module 204. Sample measurements may then be evaluated by a data processing module 205 and, once complete, measurements may be displayed by a reporting module 206.

As stated, embodiments of the present disclosure may improve the predictive ability of MDW through combination with WBC and vital signs. This is accomplished by evaluating these measurements against predetermined criteria, which may be a range of values considered to be abnormal for a healthy adult. In some aspects, an abnormal WBC count may be equal to the SIRS criteria of a value less than 4,000/mm$^3$ (4.0×10$^3$/μL) or greater than 12,000/mm$^3$ (12.0× 10$^3$/μL). In some aspects, an abnormal WBC count may be equal to the medical definition of a value less than about 5,000/mm$^3$ and greater than about 10,000/mm$^3$. In some aspects, an abnormal MDW may be a value greater than 20.0 channels. In some aspects, an abnormal SBP may be a value less than or equal to 100 mmHg. Notably, this differs from the standard medical definition of hypotension, which is a value of or below 90 mmHg. One of skill in the art understands that these cut-offs can be modified to address, for example, specific patient sub-populations (such as cancer patients, pediatric patients, etc.) or to modify the sensitivity and/or specificity of the test (e.g., by opening a range to make it more inclusive, or further limiting a range to make it more exclusive).

In a hospital setting, there are four measurements, referred to as vital signs, which are routinely monitored by medical professionals. Vital signs are typically recorded during any hospital visit, but especially during ED triage, which is used to identify a patient's level of urgency and treatment pathway. These measurements are body temperature, pulse rate, respiration rate, and blood pressure. Body temperature can be measured in several different ways including orally, rectally, axillary (under the arm), by ear, or by skin. A normal body temperature for a healthy adult, though highly variable with respect to conditional information such as measurement method, location, or time of day and is considered to be any temperature within a range from 97.8 degrees Fahrenheit to 99.1 degrees Fahrenheit, with an average value of 98.6 degrees Fahrenheit. A higher than normal body temperature is called hyperthermia, or fever, and a lower than normal body temperature is called hypothermia.

"Pulse rate," or "heart rate," is a measurement of the number of times the heart beats in a minute. This can be measured by various machines or by manually pressing one's fingertips to either a patient's neck or wrist and counting the number of beats per unit time. A normal pulse rate for a healthy adult ranges from 60 to 100 beats per minute.

Respiration rate is the number of breaths one takes in one minute. This measurement can be taken by counting the number of breaths a patient takes per unit time. A normal respiration rate for a healthy adult is between 12 and 16 breaths per minute.

Blood pressure is a measurement of the pressure resulting from blood pressing against the walls of one's arteries. It is recorded as two numbers, often in millimeters of mercury (mmHg). The first number is typically systolic pressure, the pressure in the arteries resulting from the heart contracting and pushing blood into the arteries. The second number is typically diastolic pressure, the pressure in the arteries when the heart relaxes and is refilled with blood between contractions. Blood pressure can be approximated through noninvasive measurement using an instrument called a sphygmomanometer, where an inflatable cuff is placed around one's arm. The cuff inflates until the circulation in the patient's arm is reduced. At this point, the air is slowly released and the person measuring the blood pressure will listen for blood moving through the patient's artery with a stethoscope. The first sound that is heard corresponds to the systolic blood pressure (SBP), and the point that this sound goes away corresponds with the diastolic blood pressure. Blood pressure can also be measured noninvasively by other means, including automated machines. A more accurate determination of blood pressure can be obtained invasively through catheter measuring devices which may be inserted into various parts of the cardiovascular system. The average blood pressure measurement for a healthy adult is considered to be 120/80 mmHg. Low blood pressure ("hypotension") is a reading of 90/60 mmHg or lower. High blood pressure ("hypertension") is a reading of 140/90 mmHg or higher.

Other vital signs are also recognized in the medical field including: pain, measured on a 0 to 10 pain scale, oxygen saturation, measured by pulse oximetry, blood glucose level, measured in mmol/L, menstrual cycle indications, such as length and regularity, end-tidal $CO_2$ ($ETCO_2$), measured in percentage of $CO_2$ or mmHg, walking speed, measured in meters/second, altered mental status, or delirium, which may be measured by several different rating scales including the Glasgow Coma Scale (GCS), which ranges from a score of 3 to 15.

For the calculation of qSOFA, altered mental status is measured by the GCS, a scoring system used to assess a patient's level of consciousness. The GCS is measured on a 15-point scale based on eye, verbal, and motor criteria where a lower score is associated with the most severe brain dysfunction. The eye response is scored from 1-4, where no eye opening is given a score of 1 and spontaneous eye response is given a score of 4. Verbal response is measured from 1-5, no verbal response (1) to an oriented verbal response (5). Motor response is measured from 1-6, no motor response (1) to obeys command (6). A GCS score of 8 points or less is associated with severe brain dysfunction or injury, a GCS score of 9 to 12 is associated with moderate brain dysfunction or injury, and a GCS score of 13 to 14 is associated with mild brain dysfunction or injury, and a score of 15 is considered normal. The qSOFA criteria for altered mental status includes any GCS score below 15.

"Patient" can refer to any individual currently receiving medical care, a person in need of medical care, a person waiting to receive medical care, or a person who has already received medical care. "Patient" does not necessarily mean that the individual is suffering from any condition and can include individuals receiving routine health examinations. Patient refers to individuals in a hospital setting, in long term care facilities, nursing homes, emergency vehicles, in-home care settings, urgent care facilities and anywhere else that a person may receive medical attention from a trained professional. A trained professional may include physicians, nurses, therapists, physician assistants, hospice workers, emergency medical technicians, and any other trained caregivers. Patients hospitalized for less than 24 hours may also be referred to as "outpatients," while those staying at a hospital for more than 24 hours may be referred to as "inpatients."

Patient information is typically stored in a patient medical record, or EMR (also referred to as EHR). This information can include SIRS measurements, qSOFA measurements, and vital signs recorded during ED triage. The EMR may collect this information directly from a medical device, or measurements may be manually entered into the EMR by a medical professional.

WBC is a test that measures the number of white blood cells, also called leukocytes, in a patient's body. These cells are important for fighting infections in a body, and an increased WBC number can indicate infection or other underlying conditions in the body, in some instances before a patient presents clinical symptoms or when a patient presents ambiguous clinical symptoms. A normal WBC count for a healthy adult can vary between about 5,000 to 10,000 white blood cells per microliter (μl or mcL) or cubic millimeter ($mm^3$) of blood. This is different from the normal count defined by SIRS criteria (4,000 to 12,000 WBC/mcL).

Sub-types of white blood cells may be measured as a differential (CBC-diff), with each sub-type being within a typical percentage of the total WBC: neutrophil (55 to 73 percent), lymphocyte (20 to 40 percent), eosinophil (1 to 4 percent), monocyte (2 to 8 percent), and basophil (0.5 to 1 percent).

Measuring a patient's WBC can require a blood draw, otherwise known as a venipuncture. This procedure, often performed by a phlebotomist, involves the insertion of a small needle into a patient's vein and collecting blood into a 3 ml to 10 mL tube. This blood tube may then be transferred to an automated machine that will analyze the sample to determine the number of white blood cells, an embodiment of which is depicted in FIG. 2. In an automated embodiment, in addition to the percentage of each white blood cell type, it is possible to obtain detailed morphological information about the blood cells, such as volume and size. This automated measurement may be based on the direct current (DC) impedance measured from cells in a blood sample. This traditional method, also known as the Coulter Principle, is accomplished by an analyzer through passing an electric current through a blood sample and measuring the number of individual cells based on a change in impedance resulting from the cells passing through a measurement module. Another automated method is a laser flow cytometry system which transmits light through a blood sample. One or more absorption signals are measured, and the resulting light scatter is measured at different angles to determine cell morphology. Another method is fluorescent flow cytometry, which works like flow cytometry but, with the addition of fluorescent reagents, has an extended capability of measuring more specific cell populations and more specific morphological information, such the nucleus-to-plasma ratio of certain cells. Imaging is another method and involves a camera which automatically collects images of stained cells and can use image processing and pattern-recognition techniques to classify the cells automatically or present detailed cell images to a professional for review. Cell count and morphology information may also be measured manually, by a medical professional, by transferring a blood sample to a microscope slide, staining the slide, and making a visual morphology evaluation and cell count. This process involves placing a drop of blood onto a slide and using a "spreader slide" to disperse the blood across the slide so that the blood cells are sufficiently far apart to be manually differentiated. Once the blood, also referred to as blood film, is fixed to the slide, typically through immersion in methanol, it may be stained. Routine blood analysis is typically performed on blood films stained with Romanowsky stains, which allow for the detection of cell types and morphology.

MDW is the standard deviation of monocyte volume. A monocyte is a type of white blood cell. The monocyte volume measurement may be determined by passing an electric current through a blood sample and measuring the volume of individual cells passing through a measurement module based on measuring the amplitude of the resulting impedance measurement. This volume may also be measured by a system which transmits light through a blood sample and measures the resulting light scatter to determine cell volume. Methods to detect the presence of sepsis and/or SIRS using WBC population data, including MDW, have been described, for example, in U.S. Provisional Application No. 62/288,091, filed Jan. 28, 2016; PCT Application No. PCT/US2017/014708, filed Jan. 24, 2017; and Park, D.-H., "Screening of sepsis using leukocyte cell population data from the Coulter automatic blood cell analyzer DxH800," Int. Jnl. 15 Lab. Hem., 2011, 33, 391-399, the contents of all of which are incorporated by reference for all purposes.

Analyzer information can be stored directly on an analyzer's software system or collected by a LIS. A LIS is a software-based laboratory information management system and is involved with inputting, processing, and storing a variety of information from analyzers throughout the lab as well as patient information. This includes the processing and storage of patient sample measurements, such as MDW or WBC. A LIS may also gather patient information from an EMR, such as vital sign measurements as well as completed patient sample measurements from an analyzer. This information may be combined with the information in the LIS and analyzed by the software to make disease state predictions. This analysis may be executed by evaluating whether selected measurements meet a predetermined criterion. Based on which predetermined criteria is met for the inputted measurements, the probability that a patient will develop sepsis may be determined. A prediction report or alert may be sent to a medical professional so that they may decide how to best treat a patient.

EXAMPLES

Embodiments of the present disclosure were tested on 2158 adult subjects aged 18-89 years old who had a CBC with differential test ordered upon presentation to the ED, SIRS and qSOFA criteria tested, and remained in the hospital for at least 12 hours. Vital sign and blood measurements associated with these patients were made during early ED triage, within the first 12 hours of presentation. Table 1 shows the test values observed, and the predetermined ranges that were used to evaluate whether a patient's measurements were normal or abnormal. The WBC data was obtained from a SIRS test, and the normal range referred to herein is consistent with the SIRS criteria definition.

TABLE 1

Predetermined ranges for MDW, WBC, and SBP which determine whether the value is "normal" or "abnormal"

|  | MDW | WBC values from SIRS score presenting to ED | SBP |
|---|---|---|---|
| Normal | ≤20.0 channels | ≥4.0 and ≤12.0 × $10^3/\mu L$ | >100 mmHg |
| Abnormal | >20.0 channels | <4.0 or >12.0 × $10^3/\mu L$ | ≤100 mmHg |

Table 2A shows the positive likelihood ratio (LR+) and post-test sepsis probability based on whether MDW and WBC values were within a predetermined range. Likelihood ratios are used in diagnostic testing to assess the value of performing a given test. LR+ evaluates the ratio of sensitivity versus specificity (sensitivity/1-specificity), and the result indicates the probability that the test result is correct. For further definition, sensitivity is the ratio of TP versus the total of combined TP and false negative (FN) results (TP/TP+FN). Specificity is the ratio of true negative results (TN) vs the total of combined TN and FP results (TN/TN+FP).

LR scores range from zero to infinity. The higher the score, the more likely it is that a person has a condition. A value equal to 10 would indicate a patient is 10 times more likely that the patient has a condition than not. Values from 0 to 1 have decreased evidence for the disease, meaning, the closer to zero the more unlikely it is that the patient has the given condition. A value equal to 1 has no diagnostic value. Clinically, values between 1 and 2 indicate a minimal increase of disease likelihood, values between 2 and 5 indicates a small increase of disease likelihood, values between 5 and 10 signify a moderate increase in disease likelihood, and values greater than 10 signify a large, and often conclusive, increase in disease likelihood.

Table 2A shows that a patient with both normal WBC and MDW are unlikely to have sepsis, which is supported by a low LR+ and a post-test probability of 2.83%. In this example, the initial (pre-test) sepsis prevalence, as determined by the embodiments of the present disclosure, was 17.8%. By evaluating MDW and WBC together, this test provided a sepsis probability evaluation of 64%, and a LR+ of 8.21 if a patient expressed abnormal MDW and WBC values. Table 2B shows detailed results, including LR+ confidence intervals.

TABLE 2A

Diagnostic statistics in determining sepsis using MDW and WBC

| Legend: | Test | LR+ | Pre-Test: 17.80% Post-test Sepsis Probability (%) |
|---|---|---|---|
| 0 = Normal | MDW = 0, WBC = 0 | 0.13 | 2.83 |
| 1 = Abnormal | MDW = 1, WBC = 0 | 1.06 | 18.69 |
| | MDW = 0, WBC = 1 | 1.46 | 24.08 |
| | MDW = 1, WBC = 1 | 8.21 | 63.99 |

TABLE 2B

Diagnostic statistics in determining sepsis using MDW and WBC including LR+ confidence intervals and detailed data.

| Test | True Positive | False Negative | True Negative | False Positive | LR+ | 95% Confidence Intervals LR + Lower | LR + Upper |
|---|---|---|---|---|---|---|---|
| MDW = 0, WBC = 0 | 31 | 354 | 713 | 1060 | 0.13 | 0.10 | 0.19 |
| MDW = 1, WBC = 0 | 89 | 296 | 1387 | 386 | 1.06 | 0.87 | 1.30 |
| MDW = 0, WBC = 1 | 69 | 316 | 1556 | 217 | 1.46 | 1.14 | 1.88 |
| MDW = 1, WBC = 1 | 196 | 189 | 1663 | 110 | 8.21 | 6.68 | 10.08 |

Table 3A shows the diagnostic statistics when evaluating SBP in addition to MDW and WBC. With the inclusion of abnormal SBP (<100 mmHg), the post-test sepsis probability increased to 76% and the LR+ increased 14.74, signifying a large and often conclusive increase in disease likelihood. Combining abnormal SBP and WBC measurements was also an improvement over combining abnormal WBC and MDW alone. In this case, there was an increase in post-test probability from 62% to 67% and, while both LR+ scores signified a moderate increase in disease likelihood, there was an increase from 7.55 to 9.21. Table 3B shows detailed results, including LR+ confidence intervals.

TABLE 3A

Diagnostic statistics in determining sepsis using MDW, WBC, and SBP versus SIRS

| Legend: | Test | LR+ | Pre-Test: 17.8% Post-test Sepsis Probability (%) |
|---|---|---|---|
| 0 = Normal | MDW = 0, WBC = 0, SBP = 0 | 0.13 | 2.7 |
| 1 = Abnormal | MDW = 1, WBC = 0, SBP = 0 | 0.9 | 16.33 |
| Asterisk (*) indicates Insufficient Data Points (≤2 data point) | MDW = 0, WBC = 1, SBP = 0 | 1.28 | 21.72 |
| | MDW = 1, WBC = 1, SBP = 0 | 7.55 | 62.06 |
| | *MDW = 0, WBC = 0, SBP = 1 | 0.48 | 9.5 |
| | MDW = 1, WBC = 0, SBP = 1 | 4.35 | 48.5 |
| | MDW = 0, WBC = 1, SBP = 1 | 9.21 | 66.61 |
| | MDW = 1, WBC = 1, SBP = 1 | 14.74 | 76.14 |

TABLE 3B

Diagnostic statistics in determining sepsis using MDW, WBC, and SBP versus SIRS including LR+ confidence intervals and detailed data.

| Legend: | Test | True Positive | False Negative | True Negative | False Positive | LR+ | 95% Confidence Intervals | |
|---|---|---|---|---|---|---|---|---|
| | | | | | | | LR + Lower | LR + Upper |
| 0 = Normal | MDW = 0, WBC = 0, SBP = 0 | 29 | 356 | 732 | 1041 | 0.13 | 0.09 | 0.18 |
| 1 = Abnormal | MDW = 1, WBC = 0, SBP = 0 | 72 | 313 | 1405 | 368 | 0.90 | 0.72 | 1.13 |
| Asterisk (*) | MDW = 0, WBC = 1, SBP = 0 | 59 | 326 | 1561 | 212 | 1.28 | 0.98 | 1.67 |
| indicates | MDW = 1, WBC = 1, SBP = 0 | 164 | 221 | 1673 | 100 | 7.55 | 6.04 | 9.44 |
| Insufficient | *MDW = 0, WBC = 0, SBP = 1 | 2 | 383 | 1754 | 19 | 0.48 | 0.11 | 2.07 |
| Data Points | MDW = 1, WBC = 0, SBP = 1 | 17 | 368 | 1755 | 18 | 4.35 | 2.26 | 8.36 |
| (≤2 data | MDW = 0, WBC = 1, SBP = 1 | 10 | 375 | 1768 | 5 | 9.21 | 3.17 | 26.79 |
| point) | MDW = 1, WBC = 1, SBP = 1 | 32 | 353 | 1763 | 10 | 14.74 | 7.31 | 29.72 |

Table 4A shows the results when other normal SIRS criteria were incorporated.

With MDW and WBC alone, and all SIRS criteria being normal, the post-test sepsis probability prediction was 29%, with an LR+ of 1.91. An LR+score between 1 and 2 is recognized as a minimal increase in disease likelihood. In this scenario, even while accounting for other SIRS criteria being in the normal healthy range, an abnormal SBP value combined with abnormal MDW and WBC resulted in a post-test sepsis probability evaluation of 61.47% and an LR+ of 7.37, signifying a moderate increase in disease likelihood. Table 4B shows detailed results, including LR+confidence intervals.

TABLE 4A

Diagnostic statistics in determining sepsis using MDW, WBC and SBP where all other SIRS criteria are normal.

| Legend: | Based on Presenting SIRS Criteria [Initial Triage] |
|---|---|
| 0 = Normal | |
| 1 = Abnormal | |
| Asterisk (*) indicates Insufficient Data Points (≤2 data point) | Pre-Test: 17.8% |

TABLE 4A-continued

Diagnostic statistics in determining sepsis using MDW, WBC and SBP where all other SIRS criteria are normal.

| Test | LR+ | Post-test Sepsis Probability (%) |
|---|---|---|
| *MDW = 0, WBC = 0, SBP = 0, TEMP = 0, HR = 0, RR = 0 | 0.01 | 0.14 |
| MDW = 1, WBC = 0, SBP = 0, TEMP = 0, HR = 0, RR = 0 | 0.26 | 5.38 |
| MDW = 0, WBC = 1, SBP = 0, TEMP = 0, HR = 0, RR = 0 | 0.51 | 9.91 |
| MDW = 1, WBC = 1, SBP = 0, TEMP = 0, HR = 0, RR = 0 | 1.91 | 29.28 |
| *MDW = 0, WBC = 0, SBP = 1, TEMP = 0, HR = 0, RR = 0 | 0.35 | 7.12 |
| *MDW = 1, WBC = 0, SBP = 1, TEMP = 0, HR = 0, RR = 0 | 0.46 | 9.07 |
| *MDW = 0, WBC = 1, SBP = 1, TEMP = 0, HR = 0, RR = 0 | 2.3 | 33.27 |
| MDW = 1, WBC = 1, SBP = 1, TEMP = 0, HR = 0, RR = 0 | 7.37 | 61.47 |

TABLE 4B

Diagnostic statistics in determining sepsis using MDW, WBC and SBP where all other SIRS criteria are normal, including LR+ confidence intervals and detailed data.

Legend:

0 = Normal

1 = Abnormal

Asterisk (*) indicates Insufficient Data Points (≤2 data point)

| Test | True Positive | False Negative | True Negative | False Positive | LR+ | 95% Confidence Intervals LR + Lower | LR + Upper |
|---|---|---|---|---|---|---|---|
| *MDW = 0, WBC = 0, SBP = 0, TEMP = 0, HR = 0, RR = 0 | 1 | 384 | 1073 | 700 | 0.01 | 0.00 | 0.05 |
| MDW = 1, WBC = 0, SBP = 0, TEMP = 0, HR = 0, RR = 0 | 11 | 374 | 1580 | 193 | 0.26 | 0.14 | 0.48 |
| MDW = 0, WBC = 1, SBP = 0, TEMP = 0, HR = 0, RR = 0 | 15 | 370 | 1637 | 136 | 0.51 | 0.30 | 0.86 |
| MDW = 1, WBC = 1, SBP = 0, TEMP = 0, HR = 0, RR = 0 | 22 | 363 | 1720 | 53 | 1.91 | 1.18 | 3.10 |
| *MDW = 0, WBC = 0, SBP = 1, TEMP = 0, HR = 0, RR = 0 | 1 | 384 | 1760 | 13 | 0.35 | 0.05 | 2.70 |
| *MDW = 1, WBC = 0, SBP = 1, TEMP = 0, HR = 0, RR = 0 | 1 | 384 | 1763 | 10 | 0.46 | 0.06 | 3.59 |
| *MDW = 0, WBC = 1, SBP = 1, TEMP = 0, HR = 0, RR = 0 | 1 | 384 | 1771 | 2 | 2.30 | 0.21 | 25.33 |
| MDW = 1, WBC = 1, SBP = 1, TEMP = 0, HR = 0, RR = 0 | 8 | 377 | 1768 | 5 | 7.37 | 2.42 | 22.40 |

Improvements to sepsis probability assessments were also observed when incorporating other vital sign measurements with MDW. Table 5 shows the finding that the odds of sepsis diagnosis, as defined by Sepsis-3, increase by 4 times when an abnormal MDW, is combined various qSOFA parameters, in comparison to a normal MDW. In this scenario, sepsis was defined by Sepsis-3 criteria as qSOFA was developed for the Sepsis-3 definition.

TABLE 5

Demonstration of the added value of MDW in combination with qSOFA vital sign criteria.

| Sepsis 3 & qSOFA | No qSOFA | 1 qSOFA | 2 qSOFA | 3 qSOFA | Total |
|---|---|---|---|---|---|
| Total patients | 1707 | 398 | 50 | 3 | 2158 |
| Sepsis patients (#) | 135 | 79 | 26 | 3 | 243 |
| Sepsis probability, MDW unknown | 5.6% | 14.5% | 42.6% |  | 8.0% |
| Sepsis probability, MDW normal | 3.0% | 7.2% | 29.1% |  | 4.0% |
| Sepsis probability, MDW abnormal | 10.8% | 25.0% | 49.5% |  | 15.5% |
| Sepsis odds (MDW abnormal/normal) | 3.6 | 3.5 | 1.7 |  | 3.9 |
| Probability odds of sepsis patientsat pre-test = .08 |  |  |  |  |  |

Table 6 shows the finding that the odds of sepsis-2 diagnosis increase by 6 times when an abnormal MDW, in comparison to normal MDW, is combined with any number of SIRS criteria. In this scenario, sepsis was defined by Sepsis-2 criteria as SIRS was developed for the Sepsis-2 definition.

TABLE 6

Demonstration of the added value of MDW in combination with SIRS vital sign criteria.

| Sepsis 2 & SIRS | No SIRS | 1 SIRS | 2 SIRS | 3 SIRS | 4 SIRS | Total |
|---|---|---|---|---|---|---|
| Total patients | 930 | 799 | 341 | 79 | 9 | 2158 |
| Sepsis patients (#) | 14 | 112 | 190 | 61 | 8 | 385 |
| Sepsis probability, MDW unknown | 0.6% | 6.1% | 33.5% | 57.6% | 76.2% | 8.0% |
| Sepsis probability, MDW normal | 0.1% | 3.0% | 18.0% | 28.6% | 0.0% | 3.0% |
| Sepsis probability, MDW abnormal | 2.3% | 11.8% | 48.3% | 76.6% |  | 18.7% |
| Sepsis odds (MDW abnormal/normal) | 20.6 | 3.9 | 2.7 | 2.7 |  | 6.2 |
| Probability odds of sepsis patients at pre-test = .08 |  |  |  |  |  |  |

Figure 3A:
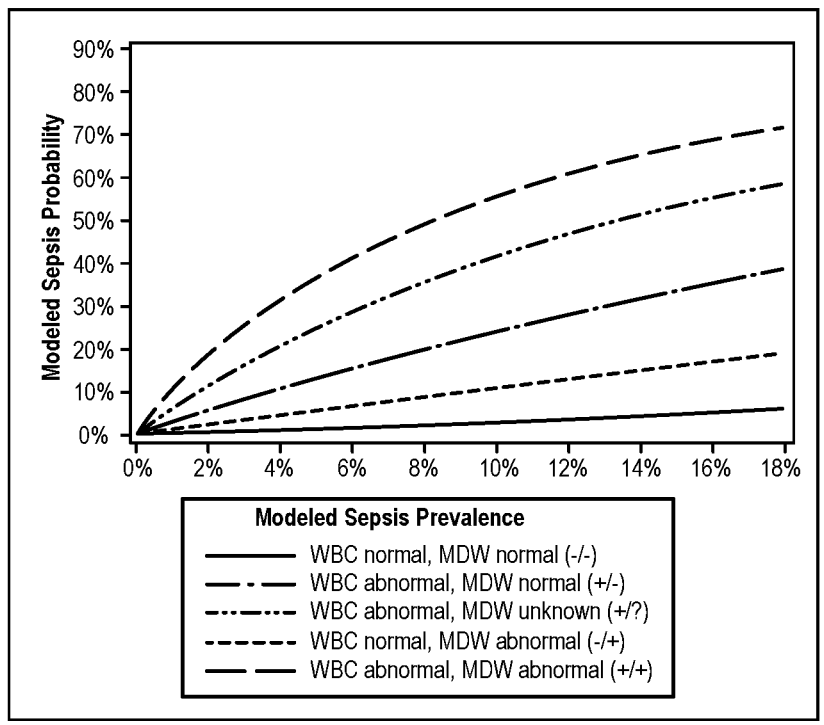
FIGS. 3A-3D provide charts exemplifying the added improvement of MDW to early sepsis detection when combined with each SIRS vital sign criterion and certain combinations of SIRS vital sign criterion.
Figure 3B:
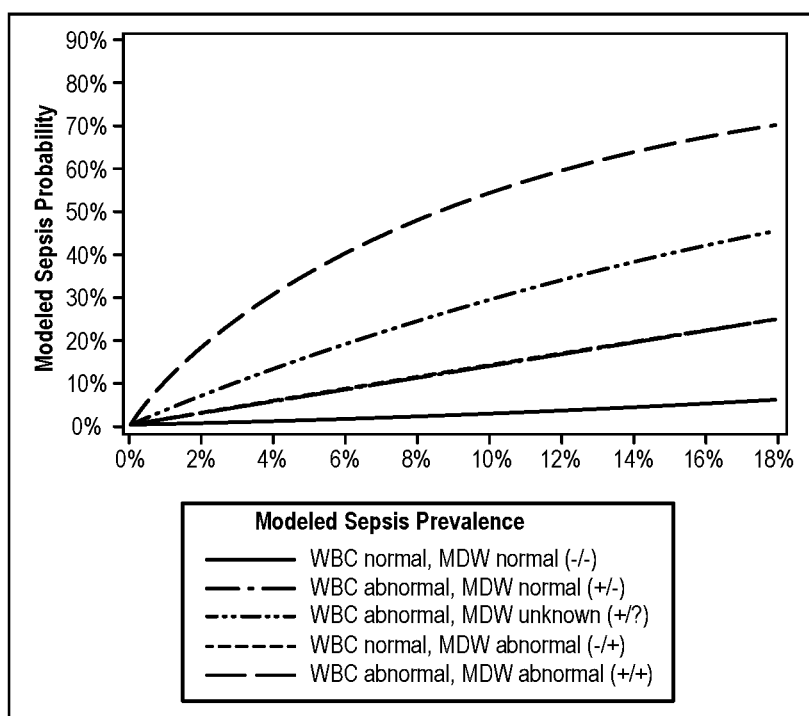
Figure 3C:
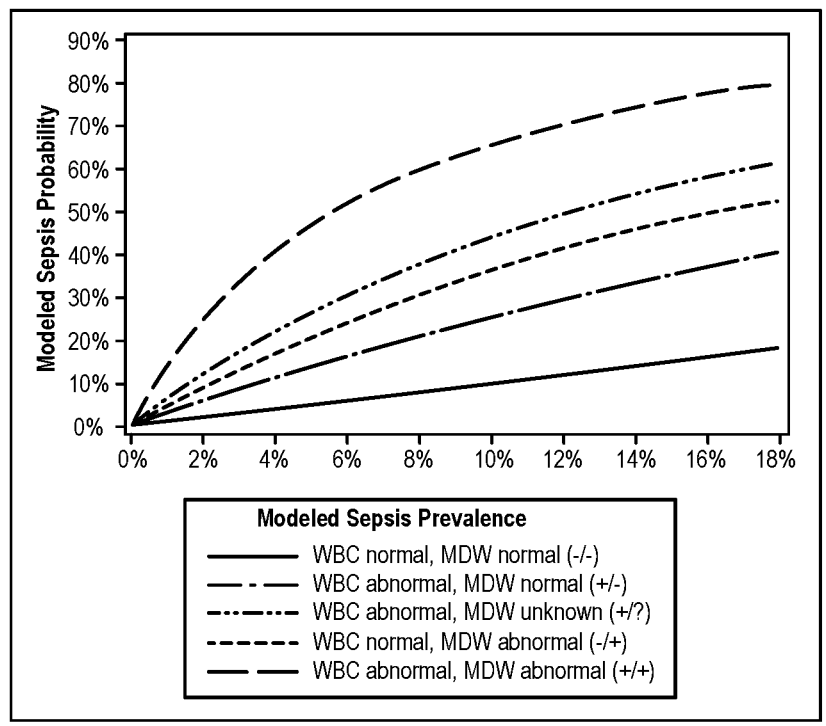
Figure 3D:
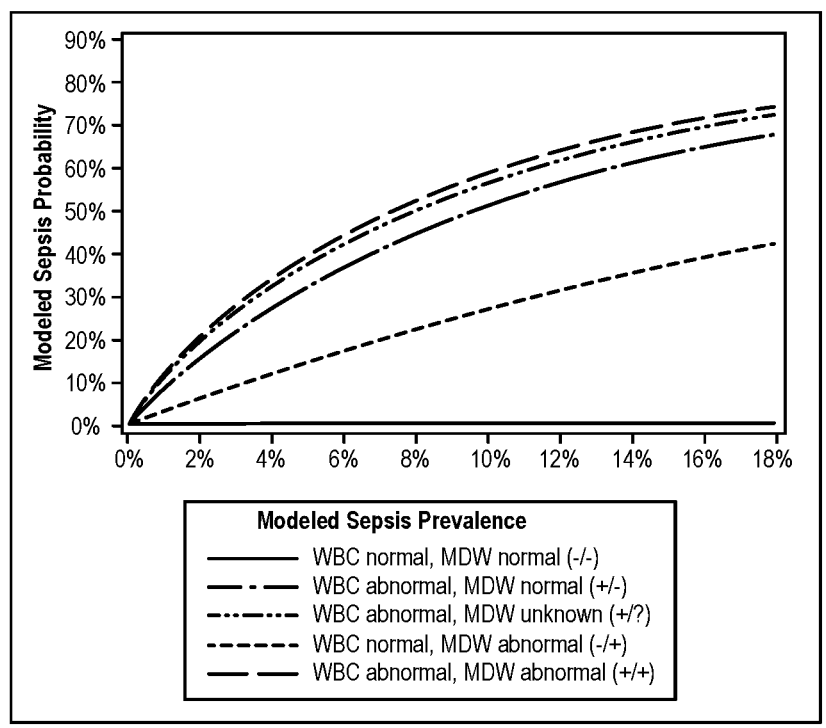

FIGS. 3A-3D further show how improvements in sepsis detection are also observed when MDW and WBC are used in combination with specific SIRS vital sign criteria. MDW and WBC improves early sepsis detection when combined with abnormal vital signs of tachycardia (FIG. 3A), tachypnea (FIG. 3B), both tachycardia and tachypnea (FIG. 3C), or abnormal temperature (FIG. 3D). The highest probability of sepsis occurs when there is a combination of abnormal MDW, abnormal WBC, and one or more abnormal (SIRS) vital signs criterion.

Figure 4A:
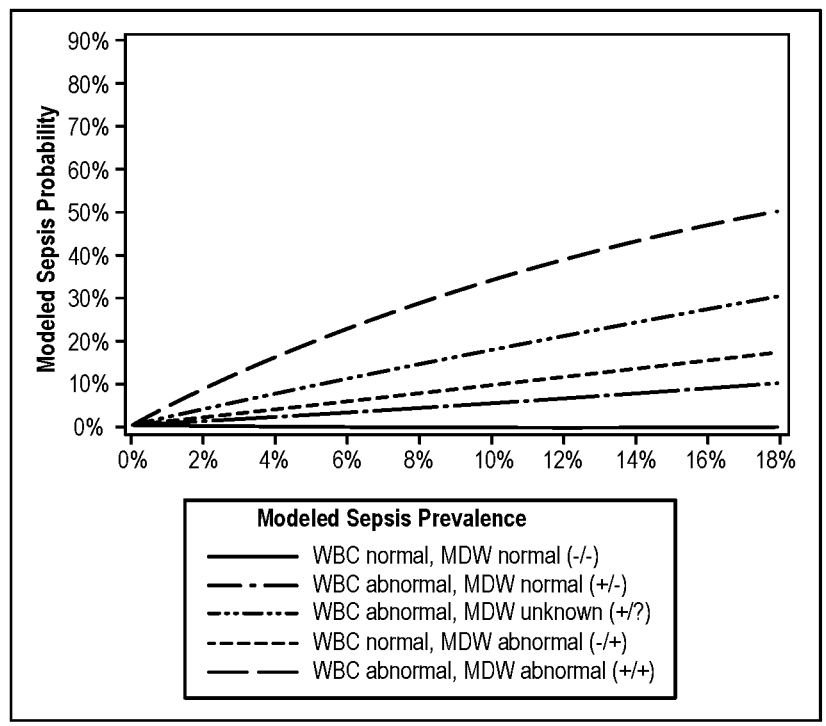
FIGS. 4A-4B provide charts exemplifying the added improvement of MDW to early sepsis detection when combined with qSOFA vital sign criterion of altered mental status and blood pressure.
Figure 4B:
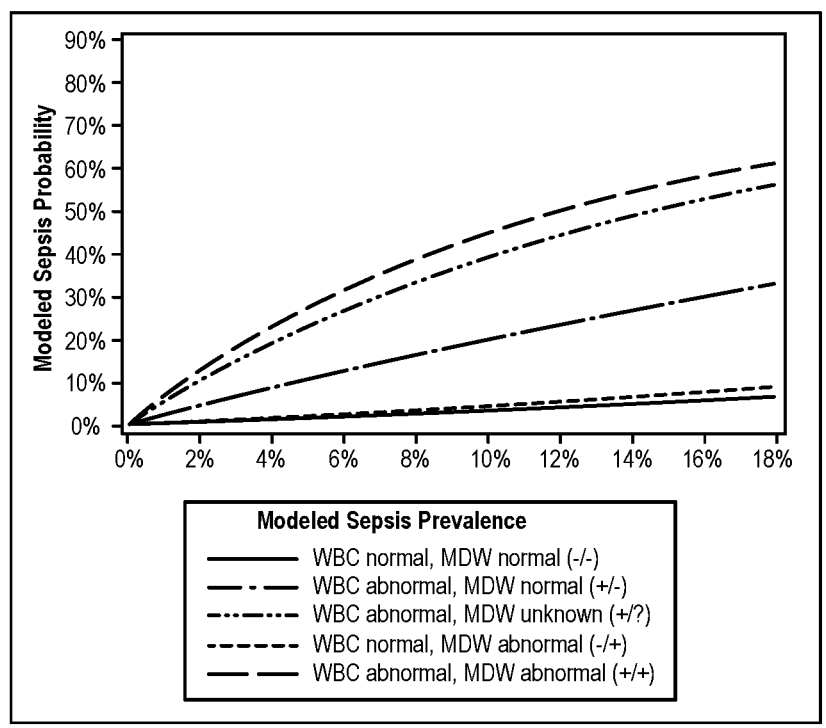

FIGS. 4A-4B exemplify that MDW and WBC in combination with the qSOFA vital sign criteria of altered mental status (FIG. 4A) and blood pressure (FIG. 4B), also markedly improves sepsis detection. In these scenarios, the highest probability of sepsis occurs when both MDW and WBC are also abnormal.

Figure 5:
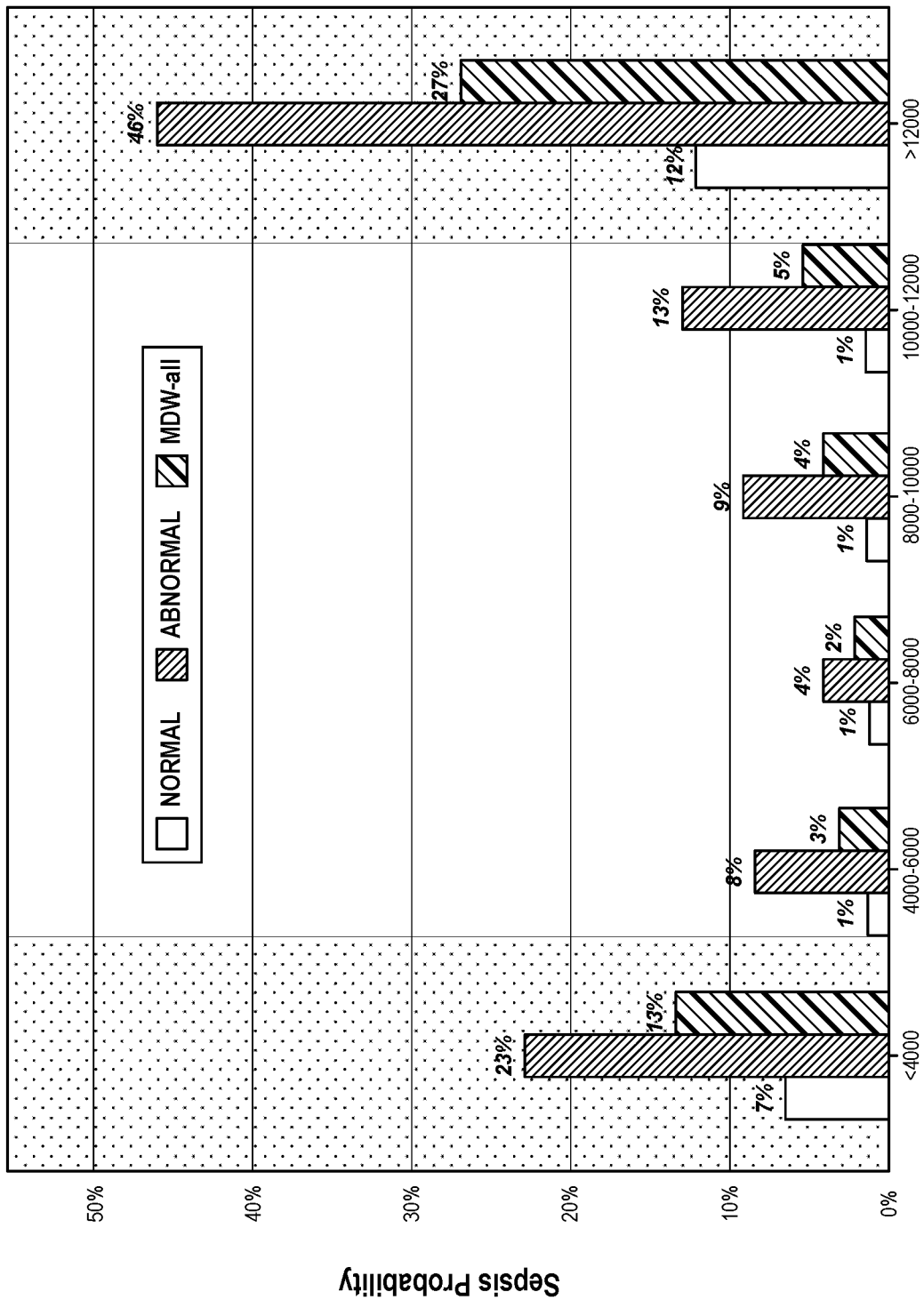
FIG. 5 provides a chart exemplifying the improvement of sepsis detection when incorporating MDW, including when WBC is normal.

FIG. 5 shows the finding that MDW actually improves detection of sepsis in ED patients across a range of WBC values, including when WBC is normal. The shaded areas in this figure indicate abnormal WBC measurements.

These scenarios exemplify the added value of incorporating SBP measurements and other vital sign measurements with WBC and MDW. Various modifications to this embodiment may be used without departing from the essence of the invention.

The dimensions and values disclosed herein are not to be understood as being strictly limited to the exact numerical values recited. Instead, unless otherwise specified, each such dimension is intended to mean both the recited value and a functionally equivalent range surrounding that value to include at least the variability due to the reproducibility of measurements made using the test methods described herein, or industry-standard test methods if no test method is expressly disclosed.

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

We claim:

1. A method of assessing a probability that a patient associated with a blood sample will develop sepsis comprising:
   a. automatically obtaining, from at least one electronic medical record, one or more vital signs;
   b. obtaining a set of patient measurements comprising white blood cell count (WBC), monocyte distribution width (MDW) based on analyzing the blood sample using a hematology analyzer adapted to capture measurements of blood cells comprised by the blood sample in a measurement module;
   c. storing the set of patient measurements and the one or more vital signs at a laboratory information system;
   d. via the laboratory information system, based on execution of a set of instructions stored on a non-transitory computer readable medium, performing acts comprising:
      i. detecting a sepsis predictive combination in the set of patient measurements by comparing at least one of the one or more vital signs and one or more hematology parameters from the set of patient measurements with respective predetermined criteria; and
      ii. providing the probability that the patient will develop sepsis when the sepsis predictive combination is detected in the set of patient measurements.

2. The method of claim 1, wherein the at least one of the one or more vital signs is blood pressure.

3. The method of claim 2, wherein the blood pressure is systolic blood pressure (SBP).

4. The method of claim 3, wherein the predetermined criteria for SBP is a value of or below about 100 mmHg.

5. The method of claim 1, wherein
   a. at least one measurement from the set of patient measurements is inputted from an electronic medical record; and
   b. at least one measurement from the set of patient measurements is inputted from an analyzer.

6. The method of claim 1, wherein:
   a. the one or more hematology parameters comprises MDW; and
   b. the predetermined criteria for MDW is a value above 20.0 channels.

7. The method of claim 1, wherein
   a. the one or more hematology parameters comprises WBC; and
   b. the predetermined criteria for WBC is a value less than about $4.0 \times 10^3/\mu L$, or greater than about $12.0 \times 10^3/\mu L$.

8. The method of claim 1, wherein:
   a. the one or more hematology parameters comprises WBC; and
   b. the predetermined criteria for WBC is a value less than about $5.0 \times 10^3/\mu L$, or greater than about $10.0 \times 10^3/\mu L$.

9. The method of claim 1, wherein the sepsis predictive combination is, for each of three measurements from the set of patient measurements, that measurement being within a range specified by its respective predetermined criteria.

10. The method of claim 1, wherein:
    a. the at least one of the one or more vital signs is a SIRS or qSOFA vital sign measurement; and
    b. the predetermined criteria for the at least one of the one or more vital signs is a SIRS or qSOFA vital sign criteria.

11. The method of claim 1, wherein the method comprises obtaining the set of patient measurements in an assessment of the patient in the first 12 hours of patient presentation.

12. The method of claim 1, wherein the method comprises obtaining the set of patient measurements in an assessment of the patient after the first 12 hours of patient presentation.

13. The method of claim 1, wherein:
    a. the at least one of the one or more vital signs comprises systolic blood pressure; and
    b. the one or more hematology parameters comprises MDW and WBC.

14. The method of claim 13, wherein:
    a. the predetermined criteria for systolic blood pressure is a value of or below 100 mmHg;
    b. the predetermined criteria for MDW is a value above 20.0 channels; and
    c. the predetermined criteria for WBC is a value less than $4.0 \times 10^3/\mu L$, or greater than $12.0 \times 10^3/\mu L$.

15. A system for assessing a probability that a patient associated with a blood sample will develop sepsis comprising:
    a. a hematology analyzer adapted to capture measurements of blood cells comprised by the blood sample in a measurement module; and
    b. a laboratory information system comprising a processor configured with instructions stored on a non-transitory computer readable medium to, when executed, cause the processor to perform acts comprising:
       i. obtain a set of patient measurements which the hematology analyzer is adapted to generate, the set of patient measurements comprising white blood cell count (WBC), monocyte distribution width (MDW), and one or more vital signs;
       ii. detect a sepsis predictive combination in the set of patient measurements by comparing at least one of the one or more vital signs and one or more hematology parameters from the set of patient measurements with respective predetermined criteria; and
       iii. provide the probability that the patient will develop sepsis when the sepsis predictive combination is detected in the set of patient measurements.

16. The system of claim 15, wherein the at least one of the one or more vital signs is systolic blood pressure (SBP).

17. The system of claim 16, wherein the predetermined criteria for SBP is a value of or below about 100 mmHg.

18. The system of claim 15, wherein:
    a. the one or more hematology parameters comprises MDW; and b. the predetermined criteria for MDW is a value above 20.0 channels.

19. The system of claim 15, wherein
a. the one or more hematology parameters comprises WBC; and
b. the predetermined criteria for WBC is a value less than about $4.0 \times 10^3/\mu L$, or greater than about $12.0 \times 10^3/\mu L$.

20. The system of claim 15, wherein:
a. the one or more hematology parameters comprises WBC; and
b. the predetermined criteria for WBC is a value less than about $5.0 \times 10^3/\mu L$, or greater than about $10.0 \times 103/\mu L$.

21. The system of claim 15, wherein the sepsis predictive combination is, for each of three measurements from the set of patient measurements, that measurement being within a range specified by its respective predetermined criteria.

22. The system of claim 15, wherein:
a. the at least one of the one or more vital signs is a SIRS or qSOFA vital sign measurement; and
b. the predetermined criteria for the at least one of the one or more vital signs is a SIRS or qSOFA vital sign criteria.

23. The system of claim 15, wherein:
a. the one or more hematology parameters comprises WBC and MDW; and
b. the at least one of the one or more vital signs comprises systolic blood pressure.

24. The system of claim 23, wherein:
a. the predetermined criteria for systolic blood pressure is a value of or below 100 mmHg;
b. the predetermined criteria for MDW is a value above 20.0 channels; and
c. the predetermined criteria for WBC is a value less than $4.0 \times 10^3/\mu L$, or greater than $12.0 \times 10^3/\mu L$.

* * * * *